US008785431B2

(12) United States Patent
Bernhardt et al.

(10) Patent No.: US 8,785,431 B2
(45) Date of Patent: Jul. 22, 2014

(54) PRODRUGS OF (1S,9S)-9-[[(1S)-1-CARBOXY-3-PHENYLPROPYL]AMINO]OCTAHYDRO-10-OXO-6H-PYRIDAZINO[1,2-A][1,2]DIAZEPINE-1-CARBOXYLIC ACID AND THEIR USE IN TRANSDERMAL THERAPEUTIC SYSTEMS

(75) Inventors: Günther Bernhardt, Regensburg (DE); Miriam Ertel, Munich (DE); Armin Buschauer, Regensburg (DE); Jörg Nink, Holzkirchen (DE)

(73) Assignee: Hexal AG, Holzkirchen (DE)

( * ) Notice: Subject to any disclaimer, the term of this patent is extended or adjusted under 35 U.S.C. 154(b) by 0 days.

(21) Appl. No.: 14/127,622

(22) PCT Filed: Jun. 20, 2012

(86) PCT No.: PCT/EP2012/061830
§ 371 (c)(1),
(2), (4) Date: Dec. 19, 2013

(87) PCT Pub. No.: WO2012/175554
PCT Pub. Date: Dec. 27, 2012

(65) Prior Publication Data
US 2014/0147477 A1  May 29, 2014

(30) Foreign Application Priority Data
Jun. 22, 2011 (EP) .................... 11171006

(51) Int. Cl.
*A61K 31/551* (2006.01)
*A61K 9/70* (2006.01)
*C07D 487/04* (2006.01)

(52) U.S. Cl.
USPC .............................. 514/221; 540/500; 424/449

(58) Field of Classification Search
USPC .............................. 514/221; 540/500; 424/449
See application file for complete search history.

(56) References Cited

U.S. PATENT DOCUMENTS

| 4,999,370 A | 3/1991 | Rüger et al. |
| 5,620,975 A | 4/1997 | Clozel et al. |
| 6,805,878 B2 | 10/2004 | Li et al. |
| 2004/0052835 A1 | 3/2004 | Klokkers et al. |
| 2009/0162420 A1 | 6/2009 | Klokkers et al. |

FOREIGN PATENT DOCUMENTS

| AU | 616249 | 10/1991 |
| CN | 101560204 | 10/2009 |
| EP | 0094095 | 9/1990 |
| EP | 0334164 | 10/1993 |
| EP | 0524512 | 3/2004 |
| WO | 02/03970 A2 | 1/2002 |

OTHER PUBLICATIONS

Beaumont, "Design of Ester Prodrugs to Enhance Oral Absorption of Poorly Premeable Compounds: Challenges to the Discovery Scientist," Current Drug Metabolism, Bentham Science Publishcers, US, vol. 4, No. 6, Jan. 1, 2003, pp. 461-485.
International Search Report and Written Opinion issued in PCT/EP2012/061830, Oct. 9, 2012, pp. 1-2 and 1-10.
European Examination Report and European Search Report issued in European Application No. 11 171 006.7, Oct. 14, 2011, pp. 1-3 and 1-2.
Attwood, "The Design and Synthesis of the Angiotensin Converting Enzyme Inhibitor Cliazapril and Related Bicyclic Compounds," J. Chem. Soc. Perkins Trans., 1986, pp. 1011-1019.

*Primary Examiner* — Brenda Coleman
(74) *Attorney, Agent, or Firm* — Jeffrey S. Melcher; Manelli Selter PLLC

(57) ABSTRACT

The present invention relates to diester prodrugs of cilazaprilate which undergo enzymatic cleavage to release the active metabolite cilazaprilate that is used for the treatment of hypertension and congestive heart failure. Furthermore the diester prodrugs of cilazaprilate possess all the properties necessary to be topically administered, preferably via transdermal therapeutic systems.

20 Claims, 1 Drawing Sheet

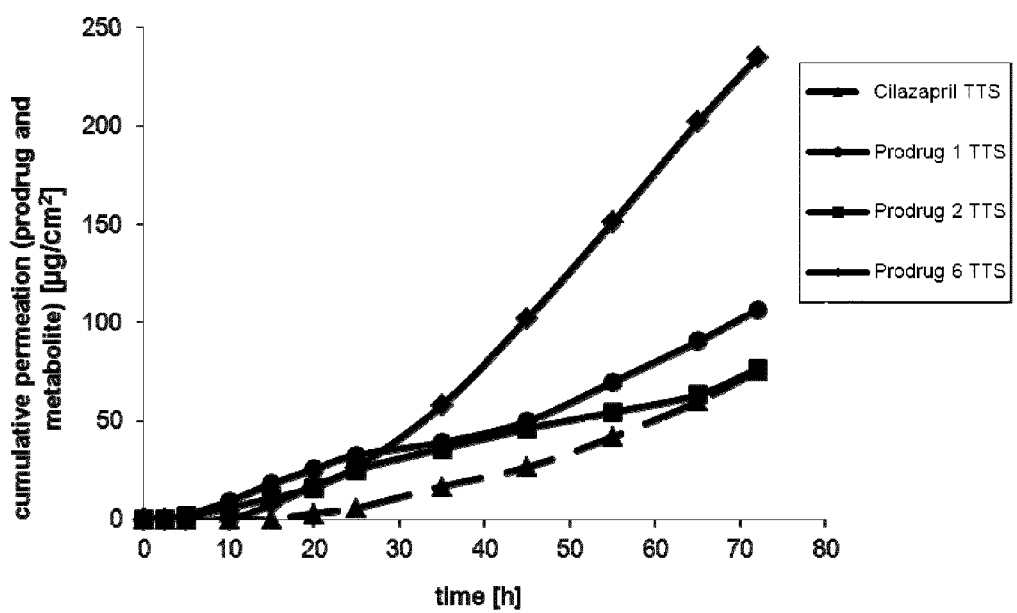

PRODRUGS OF (1S,9S)-9-[[(1S)-1-CARBOXY-3-PHENYLPROPYL]AMINO]OCTAHYDRO-10-OXO-6H-PYRIDAZINO[1,2-A][1,2]DIAZEPINE-1-CARBOXYLIC ACID AND THEIR USE IN TRANSDERMAL THERAPEUTIC SYSTEMS

This application is a National Stage Entry under 35 U.S.C. 371 of PCT/EP2012/061830, filed Jun. 20, 2012.

FIELD OF THE INVENTION

The invention relates to novel prodrugs of (1S,9S)-9-[[(1S)-1-carboxy-3-phenylpropyl]amino]octahydro-10-oxo-6H-pyridazino[1,2-a][1,2]diazepine-1-carboxylic acid and to their use in transdermal therapeutic systems.

BACKGROUND OF THE INVENTION

Angiotensin converting enzyme (ACE) inhibitors are well established cardiovascular drugs used, in particular, for the treatment of hypertension and congestive heart failure.

(1S,9S)-9-[[(1S)-1-ethoxycarbonyl-3-phenylpropyl]amino]octahydro-10-oxo-6H-pyridazino[1,2-a][1,2]diazepine-1-carboxylic acid (referred to herein as cilazapril) was first claimed in EP 0 094 095. In the same publication, cilazapril was identified as an Angiotensin Converting Enzyme (ACE) inhibitor useful in the treatment of hypertension. Cilazapril is the monoethyl ester prodrug of the corresponding dicarboxylic acid (cilazaprilate), which is the active form of the enzyme inhibitor. Cilazapril has been marketed since the early 1990's as cilazapril monohydrate by Roche under the name Dynorm® as a film coated tablet for oral administration.

A requirement in the treatment of hypertension is a sustained therapeutic drug level over a long period of time. This is not easily achieved with tablets, but can be obtained by topical delivery with a transdermal patch also commonly referred as therapeutic transdermal system (TTS). TTSs offer many other benefits in comparison with orally administered tablets, including avoidance of first pass metabolism (because the drug does not pass through the liver before reaching the systemic circulation); avoidance of gastro-intestinal side effects; the potential for zero-order drug delivery; reduced side effects (because of lower peak plasma concentrations); increased safety (by allowing the application of an accurately known dose to a clearly defined area); and improved patient compliance.

Unfortunately many orally administered drug candidates lack the necessary physicochemical properties that would allow them to permeate the skin to a clinically useful extent.

In U.S. Pat. No. 6,805,878 a transdermal therapeutic system of an ACE inhibitor such as enalapril is disclosed, wherein the flux of the drug present in the TTS is increased due to the presence of the more lipophilic derivative, enalapril ethyl ester.

In US 2009/0162420 the chemical stability problem of ACE-inhibitors in a semisolid dosage form, in particular due to the intramolecular lactam cyclisation leading to the formation of diketopiperazines, is addressed by the creation of salts of the ACE-inhibitor dicarboxylic acids with organic amines and/or with alkali compounds i.e. compounds containing an alkali metal cation.

Instability in a semisolid dosage form is also a problem with cilazapril. Although cilazapril has a more rigid structure than other ACE-inhibitors and has no distinct tendency to intramolecular cyclisation, it presents stability problems in adhesive layers of transdermal therapeutic systems as shown in Table 1.

TABLE 1

10% cilazapril in an acrylic adhesive (Durotak 87-4098, Henkel)

| Storage time | Storage conditions | assay [%] |
|---|---|---|
| 0 months | uncontrolled | 98.1 |
| 3 weeks | 25° C./60% relative humidity | 98.0 |
| 7 months | 25° C./60% relative humidity | 91.9 |
| 3 weeks | 40° C./75% relative humidity | 95.9 |
| 7 months | 40° C./75% relative humidity | 80.4 |

US 2004/0052835 discloses that stabilization of ACE-inhibitors can be achieved in a TTS by diesterification of their metabolites, the ethyl ester of the ACE-inhibitors being preferred. However, it has been found that the ethyl ester of cilazapril is stable against enzymatic cleavage. Accordingly, although it is stable within the patch, the ethyl ester of cilazapril is not transformed in vivo into the pharmacologically active form of the ACE inhibitor and therefore is not suitable for transdermal dosage forms.

Moreover for transdermal therapeutic systems there exists a further requirement. The active ingredient, that is dissolved in the adhesive layer of the TTS, must stay in solution—i.e. crystals of the active ingredient must not form on the surface of the TTS. Accordingly crystallization in a transdermal therapeutic system is a further problem which has to be overcome.

SUMMARY OF INVENTION

Surprisingly, it has been found that the diester prodrugs of cilazaprilate according to the present invention are stable within a TTS and undergo enzymatic cleavage, leading to the active metabolite cilazaprilate. Accordingly, these prodrugs are strong candidates for topical administration in transdermal therapeutic systems.

The novel prodrugs of cilazaprilate contain the partial structure of cilazapril and are additionally esterified at the heterocyclic carboxylic acid as shown in formula (A). The respective compounds are referred to herein as "cilazapril prodrugs" or "prodrugs of cilazapril", although cilazaprilate is the active ingredient.

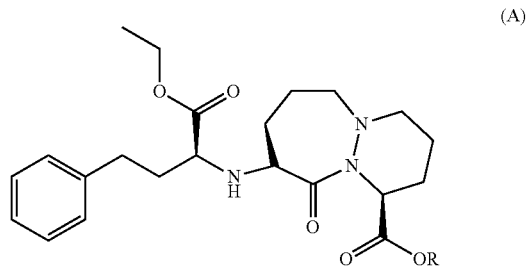

(A)

wherein the promoiety R is one of the following:
alkoxycarbonyloxyalkyl such as 1-(alkoxycarbonyloxy)ethyl,
acyloxyalkyl such as 1-(acyloxy)ethyl,
5-alkyl-2-oxo-1,3-dioxol-4-ylalkyl such as 5-alkyl-2-oxo-1,3-dioxol-4-ylmethyl,
morpholinoalkyl such as 2-morpholinoethyl,
(alkyloxycarbonyl)[4-(ethoxycarbonyl)phenyl]aminoalkyl such as (ethoxycarbonyl)[4-(ethoxycarbonyl)phenyl]aminomethyl,
or (morpholinoacetoxy)alkyl such as 1-(2-morpholinoacetoxy)ethyl.

More specifically, the promoieties of the cilazapril ester prodrugs may be the ones listed in Table 2.

TABLE 2

| Prodrug moiety | More specifically R may be | |
| --- | --- | --- |
| 1-(alkoxycarbonyloxy)ethyl | (structure) | X = ethyl (1), cyclohexyl (2), isopropyl (3) |
| 1-(acyloxy)ethyl | (structure) | X = methyl (4), tert-butyl (5) |
| morpholinoalkyl | (structure) (6) | X = $CH_2-N\underset{}{\bigcirc}O$ |
| (morpholinoacetoxy)alkyl | (structure) (7) | X = $CH_3$, Y = $CH_2$, Z = (morpholino) |
| 5-alkyl-2-oxo-1,3-dioxol-4-ylalkyl | (structure) | X = methyl (8), tert-butyl (9) |
| N-aryl-N-(alkyloxycarbonyl)aminomethyl | (structure) | X = H, Y = $CH_2CH_3$ (10)<br>X = $COOCH_2CH_3$, Y = $CH_2CH_3$ (11)<br>X = $COOCH_2CH_3$, Y = $CH_3$ (12) |

More particularly the cilazapril prodrugs are selected from:
(1S,9S)-1-(ethoxycarbonyloxy)ethyl 9-[[(1S)-1-ethoxycarbonyl-3-phenylpropyl]amino]-10-oxooctahydro-1H-pyridazino[1,2-a][1,2]diazepine-1-carboxylate,
(1S,9S)-1-(cyclohexyloxycarbonyloxy)ethyl 9-[[(1S)-1-ethoxycarbonyl-3-phenylpropyl]amino]-10-oxooctahydro-1H-pyridazino[1,2-a][1,2]diazepine-1-carboxylate,
(1S,9S)-1-(isopropyloxycarbonyloxy)ethyl 9-[[(1S)-1-ethoxycarbonyl-3-phenylpropyl]amino]-10-oxooctahydro-1H-pyridazino[1,2-a][1,2]diazepine-1-carboxylate,
(1S,9S)-1-(acetoxy)ethyl 9-[[(1S)-1-ethoxycarbonyl-3-phenylpropyl]amino]-10-oxooctahydro-1H-pyridazino[1,2-a][1,2]diazepine-1-carboxylate,
(1S,9S)-1-(2,2-dimethylpropanoyloxy)ethyl 9-[[(1S)-1-ethoxycarbonyl-3-phenylpropyl]amino]-10-oxo octahydro-1H-pyridazino[1,2-a][1,2]diazepine-1-carboxylate,
(1S,9S)-2-morpholinoethyl 9-[[(1S)-1-ethoxycarbonyl-3-phenylpropyl]amino]-10-oxooctahydro-1H-pyridazino[1,2-a][1,2]diazepine-1-carboxylate and
(1S,9S)-1-(2-morpholinoacetoxy)ethyl 9-[[(1S)-1-ethoxycarbonyl-3-phenylpropyl]amino]-10-oxooctahydro-1H-pyridazino[1,2-a][1,2]diazepine-1-carboxylate.

A second aspect of the invention relates to pharmaceutical compositions comprising the aforementioned cilazapril prodrugs, in particular transdermal therapeutic systems (TTS).

The cilazapril prodrugs may be dissolved or suspended in a pressure sensitive adhesive within the TTS. An additional adhesive layer which does not comprise a cilazapril prodrug may be present in the TTS.

Furthermore, a penetration enhancer, a permeation enhancer, a tackifier and/or a crystallization inhibitor may also be present in the adhesive layer(s).

In another aspect of the invention, the pressure sensitive adhesive may be silicon, polyacrylate and/or polyisobutylene based.

In a further aspect of the invention, the TTSs comprise a cover patch.

Finally, the cilazapril prodrugs can be used for the treatment of hypertension and congestive heart failure in pharmaceutical compositions, in particular, in TTSs.

FIGURE

FIG. 1 shows the in vitro release of a TTS comprising cilazapril and of TTSs comprising the novel cilazapril prodrugs (1), (2) or (6) through human skin.

DESCRIPTION

According to the present invention pharmaceutical compounds in the form of stabilized prodrugs of cilazapril, whose active metabolite is the dicarboxylic acid cilazaprilate, were synthesised and used in the manufacture of new transdermal therapeutic systems. The term prodrug relates to an inactive transport form of a drug that releases the active drug in vivo after chemical or enzymatic conversion.

Synthesis of Diester Prodrugs of Cilazaprilate ("Cilazapril Prodrugs")

The compounds of the present invention were prepared by analogy with known synthesis procedures. Synthesis of specific cilazapril prodrugs are provided in the example section of the description.

Metabolic Studies of the Cilazapril Prodrugs

As shown by the dotted lines in scheme 1 below, there exist two potential pathways for the hydrolysis of the cilazapril prodrugs and the formation of the active metabolite cilazaprilate. Each of the ester moieties of the cilazapril prodrugs may undergo hydrolysis.

Scheme 1: Potential Pathways for the Hydrolysis of Cilazapril Prodrugs

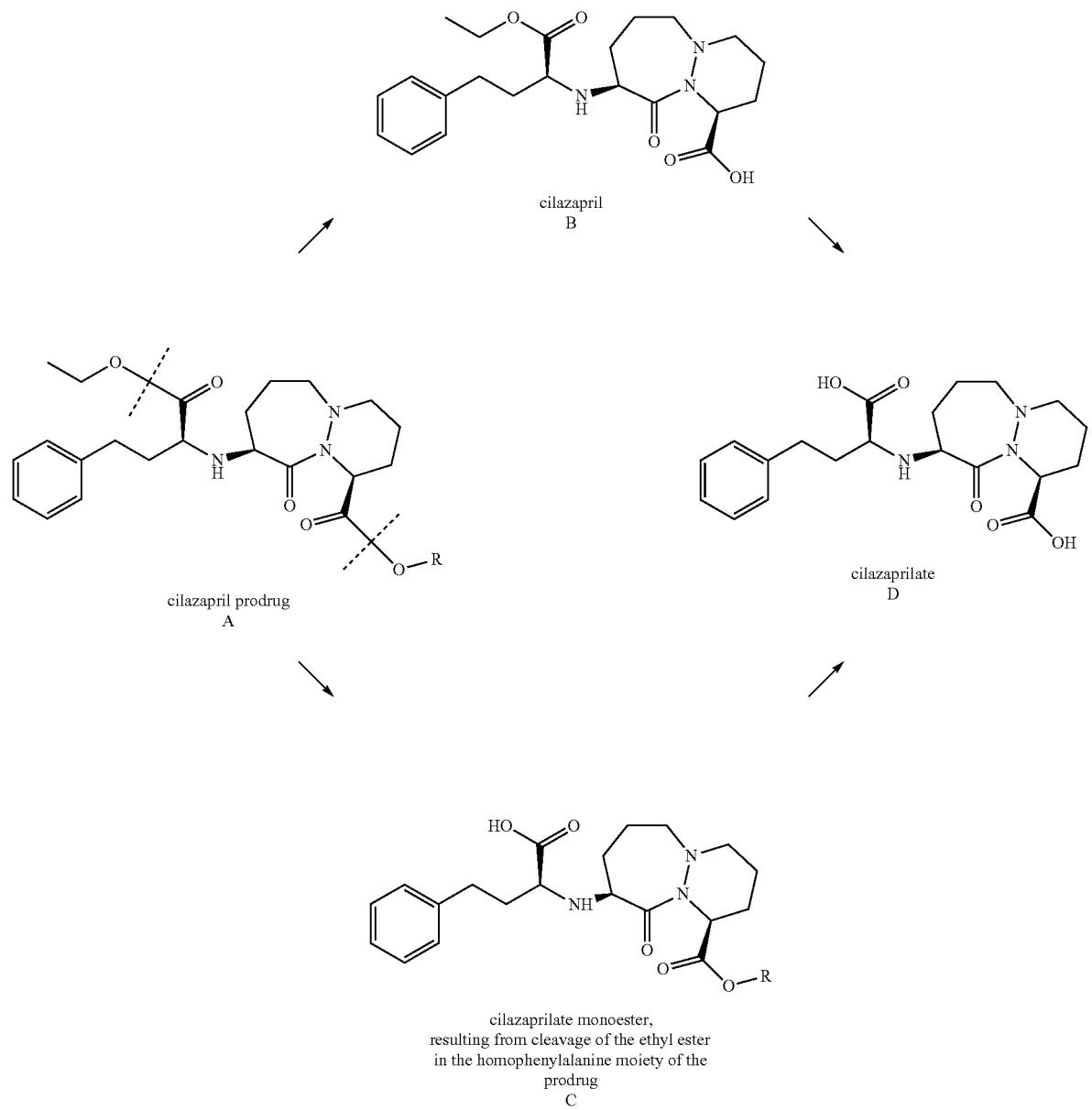

To assess whether the synthesised cilazapril prodrugs undergo enzymatic cleavage, metabolic studies were carried out in three well established incubation media for the investigation of transdermal administration.

Due to its similarities with human skin, in terms of enzyme activity and distribution, a porcine skin homogenate (25% w/w in PBS-buffer, 0.65 U/ml, 1.3 mg/ml (Bradford)) was used for the metabolic studies.

Human plasma (CPD plasma, 3.82 U/ml), which contains i.a. cholinesterase and acetylcholinesterase, was used as the second incubation media.

Buffered porcine liver esterase (suspension in 3.2 M $(NH_4)_2$ $SO_4$ solution, pH 8, 12 mg prot./ml (Biuret), 260 U/mg prot.) was chosen as the third incubation media, because porcine liver esterase mimics the carboxylesterase present in the human skin.

Incubation mixtures were prepared by adding a respective prodrug stock solution to porcine skin homogenate (PSH), human plasma and buffered porcine liver esterase (PLE), respectively. The compositions of the incubation mixtures are shown in Table 3.

TABLE 3

| | | volume (µl) | | | | stock solution in MeOH | | stock solution in DMSO | |
|---|---|---|---|---|---|---|---|---|---|
| No. | incubation mixture | phosphate buffer | porcine skin homogenate | human plasma | porcine liver esterase dilution | conc. (mM) | µl | conc. (mM) | µl |
| Cilazapril | buffer | 1960 | — | — | — | — | — | 100 | 40 |
| | PSH | — | 1960 | — | — | — | — | 100 | 40 |
| | human plasma | — | — | 1960 | — | — | — | 100 | 40 |
| | buffered PLE | 1920 | — | — | 40 | — | — | 100 | 40 |
| 1 | buffer | 1960 | — | — | — | 50 | 40 | — | — |
| | PSH | — | 1960 | — | — | — | — | 50 | 40 |
| | human plasma | — | — | 1960 | — | 50 | 40 | — | — |
| | buffered PLE | 1920 | — | — | 40 | 50 | 40 | — | — |
| 2 | buffer | 1960 | — | — | — | — | — | 50 | 40 |
| | PSH | — | 1960 | — | — | — | — | 50 | 40 |
| | human plasma | — | — | 1960 | — | 50 | 40 | — | — |
| | buffered PLE | 1920 | — | — | 40 | 50 | 40 | — | — |
| 3 | buffer | 1960 | — | — | — | 50 | 40 | — | — |
| | PSH | — | 1960 | — | — | — | — | 50 | 40 |
| | human plasma | — | — | 1960 | — | 50 | 40 | — | — |
| | buffered PLE | 1920 | — | — | 40 | 50 | 40 | — | — |
| 4 | buffer | 1960 | — | — | — | 50 | 40 | — | — |
| | PSH | — | 1960 | — | — | — | — | 50 | 40 |
| | human plasma | — | — | 1960 | — | 50 | 40 | — | — |
| | buffered PLE | 1920 | — | — | 40 | 50 | 40 | — | — |
| 5 | buffer | 1960 | — | — | — | 50 | 40 | — | — |
| | PSH | — | 1960 | — | — | — | — | 50 | 40 |
| | human plasma | — | — | 1960 | — | 50 | 40 | — | — |
| | buffered PLE | 1920 | — | — | 40 | 50 | 40 | — | — |
| 6 | buffer | 1960 | — | — | — | 50 | 40 | — | — |
| | PSH | — | 1960 | — | — | — | — | 50 | 40 |
| | human plasma | — | — | 1960 | — | 50 | 40 | — | — |
| | buffered PLE | 1920 | — | — | 40 | 50 | 40 | — | — |
| 7 | buffer | 1960 | — | — | — | — | — | 50 | 40 |
| | PSH | — | 1960 | — | — | — | — | 50 | 40 |
| | human plasma | — | — | 1960 | — | — | — | 50 | 40 |
| | buffered PLE | 1920 | — | — | 40 | — | — | 50 | 40 |
| Cilazapril ethyl ester | buffer | 1960 | — | — | — | 50 | 40 | — | — |
| | PSH | — | 1960 | — | — | — | — | 50 | 40 |
| | human plasma | — | — | 1960 | — | 50 | 40 | — | — |
| | buffered PLE | 1920 | — | — | 40 | 50 | 40 | — | — |

All samples were incubated in a water bath at 37° C. After 72 h samples of the incubation mixtures (200 µl) were collected. To all samples 400 µl of ice-cold acetonitrile were added. After vortex mixing the samples were allowed to stand in a refrigerator for approx. 30 min. The samples were then centrifuged at 13000 rpm (13000 g) for 5 min. The supernatants were collected and stored at −78° C. until HPLC analysis. To 200 µl of each supernatant 400 µl of aqueous 0.05% trifluoroacetic acid were added prior to injection.

The kinetics of the hydrolysis of the cilazapril prodrugs in the different incubation media was analysed by HPLC or HPLC-MS.

The rate of hydrolysis of cilazapril, of some cilazapril prodrugs and cilazapril ethyl ester in porcine skin homogenate, human plasma and buffered porcine liver esterase at 37° C. are presented in Table 4.

TABLE 4

| compound | porcine skin homogenate | | human plasma | | porcine liver esterase | |
|---|---|---|---|---|---|---|
| | $t_{1/2}$ (h) | $f_{50\%}$ (h)a | $t_{1/2}$ (h) | $f_{50\%}$ (h) | $t_{1/2}$ (h) | $f_{50\%}$ (h) |
| cilazapril | 9.4 | 9.4 | 88.8 | 88.8 | 3.3 | 3.3 |
| 1 | 0.43 | 13.0 | 0.58 | 154 | 0.67 | 23.5 |
| 2 | 1.4 | 8.6 | 3.2 | 228 | 4.2 | 62.2 |
| 3 | 1.0 | 11.3 | 1.9 | 108 | 1.5 | 14.2 |
| 4 | 0.50 | 14.0 | 0.68 | 91.2 | 0.63 | 9.7 |
| 5 | 1.0 | 11.5 | 5.1 | 33.6 | 3.8 | 16.3 |
| 6 | 0.50 | 6.3 | 1.3 | 10.8 | 0.95 | 7.5 |
| 7 | 0.33 | 24.3 | 0.83 | 132 | 0.77 | 29.3 |
| cilazapril ethyl ester | 0.35 | —b | 11.9 | —b | 0.69 | —b | a $f_{50\%}$ is the time by which 50% of total cilazaprilate has been formed.
b No hydrolysis to cilazaprilate detectable.

Enzyme-containing incubation mixtures led to fast degradation of the cilazapril prodrugs, cilazapril 1-(ethoxycarbonyloxy)ethyl ester (1), cilazapril 1-(cyclohexyloxycarbonyloxy)ethyl ester (2), cilazapril 1-(isopropyloxycarbonyloxy)ethyl ester (3), cilazapril 1-(acetoxy)ethyl ester (4) and cilazapril 1-(2,2-dimethylpropanoyloxy)ethyl ester (5) (indicated by small half-lives) and to the formation of cilazaprilate as the final metabolite.

Also the presence of an ionizable morpholinoethyl moiety in cilazapril morpholinoethyl ester (6) or of an ionizable 1-(2-morpholinoacetoxy)ethyl ester moiety in cilazapril 1-(2-morpholinoacetoxy)ethyl ester (7) resulted in fast reaction kinetics concerning enzymatic hydrolysis.

In contrast, no hydrolysis to cilazaprilate was detectable in the cilazapril ethyl ester incubation mixtures.

Accordingly, compared to cilazapril ethyl ester, the cilazapril prodrugs of the present invention lead more quickly to the active drug cilazaprilate through enzymatic conversion.

Transdermal Therapeutic Systems

Transdermal therapeutic systems comprise typically at least one pressure sensitive adhesive (PSA), a backing layer, a release liner, and optionally, a coverpatch, which is either integrated in or separated from the transdermal therapeutic system.

The pressure sensitive adhesive forms part, or all, of an adhesive layer. At least one active ingredient may be dissolved or suspended in the pressure sensitive adhesive.

TTSs may comprise several adhesive layers but the active ingredient may not be present in all of these layers.

The suitable pressure sensitive adhesive (PSA) may be selected from the group consisting of silicon based polymer, polyacrylate, polyisobutylene, natural rubber, natural-rubber-like synthetic homo-, co- or block polymers, styrene/butadiene copolymer or a mixture thereof, as provided in the prior art. Preferably, silicon based polymer, polyacrylate based polymer and/or polyisobutylene based polymer are used as pressure sensitive adhesive(s).

The adhesive layer may further comprise optional components selected from penetration and/or permeation enhancers, tackifiers, solubilizers, crystallization inhibitors, liquid diluents, antioxidants, or fillers, or mixtures thereof.

The penetration and permeation enhancers may be selected from alkyl methyl sulfoxides, preferably decylmethyl sulfoxide, dimethyl sulfoxide; saturated fatty acids such as adipinic acid, caproic acid, caprylic acid, capric acid, myristic acid, lauric acid, levulinic acid, stearic acid, palmitic acid, and alkyl esters thereof such as adipic acid monoethylester; unsaturated fatty acids such as oleic acid, linoleic acid, linolenic acid, palmitoleic acid, and alkyl esters thereof, preferably oleyl oleate; saturated fatty alcohols such as myristyl alcohol, lauryl alcohol, stearyl alcohol, palmityl alcohol and cetyl alcohol; unsaturated fatty alcohols such as oleyl alcohol, palmitoleyl alcohol, elaidyl alcohol, linoleyl alcohol and linolenyl alcohol; 2,2,2-trichloroethanol; 2,2,2-trifluoroethanol; azocyclo-alkan-2-ones, preferably 1-dodecylazacycloheptan-2-one; pyrrolidones such as 2-pyrrolidone, alkyl-2-pyrrolidone and N-methylpyrrolidone; polyvinylpyrrolidone, glycols such as propylene glycol, polyethylene glycols, glycerol, dipropylene glycol, tripropylene glycol, diethylene glycol and triethylene glycol; alcohols, preferably ethanol, isopropyl alcohol, cyclohexanol; tetrahydrofurfuryl alcohol; diethyltoluamide; dimethyl formamide; dimethyl acetamide; urea; salicylic acid; ethylene glycol monomethyl ether; N,N-dialkylhydroxylamine; 1,2-isopropylidene glycerol; N,N-dialkylnicotinamide; alkylaminooxide; hyaluronidase; isopropyl myristate; saccharose monooleate; lecithins; non-ionic surfactants; cholic acid; and derivatives thereof.

Preferred penetration and permeation enhancers are fatty acid alkyl esters of saturated and/or unsaturated fatty acids, each containing from 8-18 carbon atoms or long chain (C10 to C30) aliphatic alcohols. Particularly preferred is octyldodecanol, most preferred 2-octyldodecanol.

The additional penetration and/or permeation enhancer is contained in an amount of 1 to 25% by weight, preferably 5 to 15% by weight, based upon the total weight of the adhesive layer.

The adhesive layer may comprise one or more of a tackifier to increase its adhesiveness.

Tackifiers which may be used in the adhesive layer include but are not limited to any compatible resins or mixtures thereof such as natural or modified rosins, such as gum rosin, wood rosin, tall-oil rosin, distilled rosin, hydrogenated rosin, dimerized rosin, and polymerized rosin; glycerol and pentaerythritol esters of natural or modified rosins, such as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; copolymers and terpolymers of natural terpenes, e.g., styrene/terpene and alpha methyl styrene/terpene; polyterpene resins having a softening point, as determined by ASTM method E28,58T, of 80 to 150° C.; the latter polyterpene resins generally resulting from the polymerization of terpene hydrocarbons, such as the bicyclic monoterpene known as pinene, in the presence of Friedel-Crafts catalysts at moderately low temperatures; also included are the hydrogenated polyterpene resins; phenolic modified terpene resins and hydrogenated derivatives thereof, for example the resin product resulting from the condensation, in an acidic medium, of a bicyclic terpene and phenol; aliphatic petroleum hydrocarbon resins having a Ball and Ring softening point of 70 to 135° C.; the latter resins resulting from the polymerization of monomers consisting of primarily of olefins and diolefins; also included are the hydrogenated aliphatic petroleum hydrocarbon resins; alicyclic petroleum hydrocarbon resins and the hydrogenated derivatives thereof; aliphatic/aromatic or cycloaliphatic/aromatic copolymers and their hydrogenated derivatives; and styrene resins such as styrene-alpha-methylstyrene resin; or mixtures thereof.

Preferred tackifiers include but are not limited to tackifiers selected from polybutenes; polysiloxanes; elastomeric and polymeric resins; terpene-based esters such as from β-pines; aliphatic and alkylaromatic resins; melamine formaldehyde resins; phenolic resins; hydroabietyl alcohol; synthetic resins; wood resins, preferably collophonium resin; or mixtures thereof.

In a further preferred embodiment, the tackifier is a resin, preferably selected from hydrogenated collophonium resin, styrene resin, hydrogenated petroleum hydrocarbon resin or a mixture thereof. The most preferred tackifier is a synthetic resin or wood resin such as collophonium ester, which can be hydrogenated.

The one or more tackifier is preferably contained in the adhesive layer in an amount of 10 to 70% by weight, preferably 25 to 65% by weight, more preferably 40 to 55% by weight, based upon the total weight of the adhesive layer.

The adhesive layer may further comprise one or more of a crystallization inhibitor.

The crystallization inhibitors may be present in the adhesive layer in an amount of 1 to 30% by weight, preferably 5 to 15% by weight, based upon the total weight of the adhesive layer.

Crystallization inhibitors which may be used in the adhesive layer of the transdermal therapeutic system are soluble polyvinyl pyrrolidones as commercially available under the trademark Kollidon®. These soluble polyvinyl pyrrolidones are non-crosslinked polyvinyl pyrrolidone homopolymers having a weight average molecular weight Mw of 1,000 to 3,000,000, more preferably from 100,000 to 2,000,000, most preferably from 1,000,000 to 1,500,000 as measured by gel permeation chromatography. The molecular weight of polyvinyl pyrrolidone (povidone) is usually expressed as the K-value. The polyvinyl pyrrolidone used herein preferably has a K-value of 10 to 100, most preferably from 80 to 95.

Further examples of crystallization inhibitors include, but are not limited to, cyclodextrins and cyclodextrin derivatives such as substituted cyclodextrins; 2-(2-ethoxyethoxy)ethanol, urea, methyl 2-methylprop-2-enoate, neohesperidine, alcohols and polyols such as ethanol, propan-2-ol, butanol, benzyl alcohol, ethylene glycol, propylene glycol, octyldecanol, octyldodecanol, butanediols and isomers thereof, glycerol, pentaerythritol, sorbitol, mannitol, dimethyl isosorbide, polyethylene glycol, polypropylene glycol, polyvinylalcohol; hydroxypropyl methylcellulose and other cellulose derivatives; ethers of polyethylene glycols (PEG) having an average molecular weight of about 200 to about 6000, such as tetrahydrofurfuryl alcohol PEG ether (glycofurol) or methoxy PEG; amides such as 2-pyrrolidone, 2-piperidone, s-caprolactam, N-alkylpyrrolidone, N-hydroxyalkyl pyrrolidone, N-alkylpiperidone, N-alkylcaprolactam, dimethylacetamide, and polyvinyl pyrrolidone; esters, such as ethyl propionate, tributylcitrate, acetyl triethylcitratetriethyl citrate, acetyl tributyl citrate, triethylcitratetriethyl citrate, ethyl oleate, ethyl caprylate, ethyl butyrate, triacetin, propylene glycol monoacetate, propylene glycol diacetate, ε-caprolactone and isomers thereof, δ-valerolactone and isomers thereof, p-butyrolactone and isomers thereof; and other solubilizers known in the art, such as Eudragit® E100, dimethyl acetamide, dimethyl isosorbide, N-methylpyrrolidones, monooctanoin, diethylene glycol monoethyl ether, and water. Mixtures of crystallization inhibitors may also be used.

Preferred crystallization inhibitors include triacetin, triethylcitrate, ethyl oleate, ethyl caprylate, dimethylacetamide, N-methylpyrrolidone, N-hydroxyethyl pyrrolidone, hydroxypropyl methylcellulose, hydroxypropyl cyclodextrins, ethanol, glycofurol, diethylene glycol monoethyl ether, propylene glycol, and dimethyl isosorbide. Particularly preferred crystallization inhibitors include sorbitol, glycerol, triacetin, ethyl alcohol, polyethylene glycol, glycofurol, and propylene glycol.

The backing layer of the TTS is generally made of a material that is impermeable to the active agent and other excipients of the adhesive layer. Furthermore it serves as a protective cover and support for the adhesive layer. The backing layer can be formed so that it is essentially the same size as the adhesive layer. A suitable thickness for the backing layer is from about 5 μm to about 300 μm although preference always tends towards a thinner backing layer. Accordingly the backing layer has preferably a thickness of less than about 150 μm, more preferably it is less than about 100 μm, and most preferably, less than about 50 μm. Ideally the backing layer has a thickness of greater than 5 μm and more, preferably more than 10 μm.

Materials suitable for making the backing layer may be selected from films of acrylate, acrylonitrile-butadiene-styrene, acrylonitrile (methyl methacrylate) copolymer, acrylonitrile copolymer, ethylene ethyl acrylate, ethylene methyl acrylate, ethylene vinyl acetate, ethylene vinyl acetate copolymer, ethylene vinyl alcohol polymer, ionomers, nylon (polyamide), nylon (polyamide) copolymer, polybutylene, polycarbonate, polyester, polyethylene terephthalate (PET), thermoplastic polyester copolymer, polyethylene copolymer (high density), polyethylene (high-molecular-weight, high density), polyethylene (intermediate-molecular weight, high density), polyethylene (linear, low density), polyethylene (low density), polyethylene (medium density), polyethylene oxide, polyimide, polypropylene, polypropylene (coated), polypropylene (oriented), polystyrene, polyurethane, polyvinyl acetate, polyvinyl chloride, polyvinylidene chloride and/or styrene-acrylonitrile. It is within the present invention that such films may be metallised or pigmented. Preferred materials for the manufacture of the backing layer are polyurethane, ethylene vinyl alcohol polymer and polyester.

The release liner is preferably a peelable release liner intended to protect the adhesive layer. The release liner is thus to be removed from the transdermal delivery system prior to application to the subject.

Release liners can be formed of polyester, polyethylene, polypropylene, polysiloxane, e.g. with a fluorosiliconized coating, polyacrylate, ethylene vinyl acetate, polyurethane, polyisobutene or paper. Preferably the paper is coated with silicone and/or polyethylene. A foil consisting of polyethylene terephthalate (PET) may be used, whereby, preferably, one side of the foil is siliconized or fluorosiliconized. Typically, the thickness of such release liner is from 50 to 120 μm, preferably from 60 to 100 μm. Also a combination of any of the above materials may be used in the preparation of the release liner. Moreover, the release liner can be made from the same material as the backing layer.

The TTS may additionally comprise a coverpatch. A coverpatch has the function of additionally fixing the TTS to the subject to which it is applied. The coverpatch can be made from the same material as the backing layer or release liner. The features described above for the backing layer/release liner equally apply for the coverpatch. In order to properly fix the coverpatch (and consequently also the TTS per se) adhesive materials generally known in the prior art can be employed.

The TTS of the present invention may be packed in a sachet generally known in the prior art. Preferably, the sachet contains an inlay for accommodating various additives such as oxygen or humidity absorbers, antioxidants, or mixtures thereof. More preferably, all additives necessary to improve the stability of the TTS, such as oxygen or humidity absorbers, antioxidants, etc., are contained in the inlay only, i.e. separate from the adhesive layer, in order to avoid any contact with the skin of the patient after having applied the TTS. This is particularly suitable for patients who have skin that is sensitive to the additives mentioned.

EXAMPLES

Cilazapril 1-(ethoxycarbonyloxy)ethyl ester (1), cilazapril 1-(cyclohexyloxycarbonyloxy)ethyl ester (2) and cilazapril morpholinoethyl ester (6) were selected as representative examples of the invention because of their ease of synthesis, adequate lipophilicity and fast reaction kinetics in porcine skin homogenate.

The transdermal therapeutic systems were manufactured with cilazapril 1-(ethoxycarbonyloxy)ethyl ester (1), cilazapril 1-(cyclohexyloxycarbonyloxy)ethyl ester (2) and cilazapril morpholinoethyl ester (6) and were compared with a transdermal therapeutic system comprising cilazapril as shown in the examples below.

The content of the prodrug may be from 2% to 35% by weight, especially from 10 to 15% by weight based on the adhesive layer(s) weight. The adhesive layer(s) weight is defined as the total weight of the TTS without the weights of backing layer, release liner and, if applicable, coverpatch.

The adhesive content of the adhesive layer may be from 65 to 98% by weight, especially from 85 to 90% by weight, based on the adhesive layer weight.

The stability of the prodrugs in the transdermal therapeutic system was determined after different storage times and temperatures by extraction of the transdermal therapeutic system with an organic solvent and subsequent analysis by HPLC.

Examples of Prodrug Synthesis:

The examples below illustrate without limitation the prodrugs of the present invention.

General Procedure for the Synthesis of Cilazapril (Alkoxycarbonyloxy)Ethyl Esters and Cilazapril (Acyloxy)Ethyl Ester:

$K_2CO_3$ (1.2 eq) was added to a solution of cilazapril (1eq) in dimethylformamide ($H_2O$<0.01%) and the solution was stirred for 10 min. The corresponding 1-(alkyloxycarbonyloxy)ethyl chloride or 1-chloroethyl alkanoate (1.3 eq) was added dropwise at 0° C. After stirring at room temperature overnight the reaction mixture was poured into water and extracted three times with ethyl acetate. The combined organic layers were washed with water, dried over anhydrous $MgSO_4$, filtered and evaporated under reduced pressure. The crude product was purified by flash chromatography.

Example 1 cilazapril 1-(ethoxycarbonyloxy)ethyl ester (1)

(1S,9S)-1-(ethoxycarbonyloxy)ethyl 9-[[(1S)-1-ethoxycarbonyl-3-phenylpropyl]amino]-10-oxooctahydro-1H-pyridazino[1,2-a][1,2]diazepine-1-carboxylate (1)

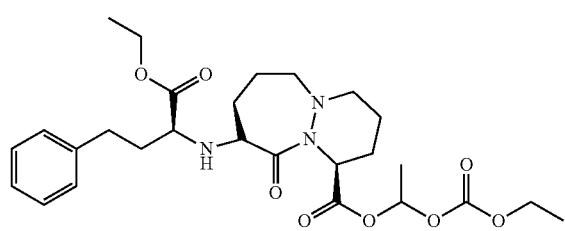

Cilazapril 1-(ethoxycarbonyloxy)ethyl ester (1) was prepared from cilazapril (2.40 mmol, 1.00 g), $K_2CO_3$ (2.88 mmol, 0.40 g) and 1-chloroethyl(ethyl)carbonate (3.12 mmol, 0.48 g) in anhydrous dimethylformamide (5 ml) following the general procedure. The desired product was obtained after flash chromatography (petroleum ether/ethyl acetate 3/2 v/v) as a yellowish oil (0.8 g, 62%).

Example 2 cilazapril 1-(cyclohexyloxycarbonyloxy)ethyl ester (2)

(1S,9S)-1-(cyclohexyloxycarbonyloxy)ethyl 9-[[(1S)-1-ethoxycarbonyl-3-phenylpropyl]amino]-10-oxooctahydro-1H-pyridazino[1,2-a][1,2]diazepine-1-carboxylate (2)

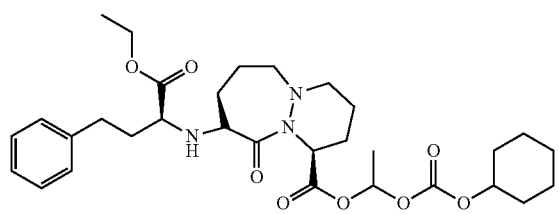

Cilazapril 1-(cyclohexyloxycarbonyloxy)ethyl ester (2) was prepared according to the general procedure using cilazapril (0.60 mmol, 0.25 g), $K_2CO_3$ (0.72 mmol, 0.10 g) and 1-chloroethyl(cyclohexyl)carbonate (0.78 mmol, 0.16 g) in anhydrous dimethylformamide (3 ml) and was obtained after flash chromatography (petroleum ether/ethyl acetate 3/2 v/v) as a yellowish oil (0.26 g, 74%).

Example 3 cilazapril 1-(isopropyloxycarbonyloxy)ethyl ester (3)

(1S,9S)-1-(isopropyloxycarbonyloxy)ethyl 9-[[(1S)-1-ethoxycarbonyl-3-phenylpropyl]amino]-10-oxooctahydro-1H-pyridazino[1,2-a][1,2]diazepine-1-carboxylate (3)

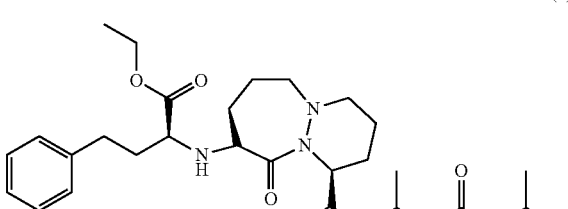

Cilazapril 1-(isopropyloxycarbonyloxy)ethyl ester (3) was prepared from cilazapril (0.60 mmol, 0.25 g), $K_2CO_3$ (0.72 mmol, 0.10 g) and 1-chloroethyl(isopropyl)carbonate (0.78 mmol, 0.13 g) in anhydrous dimethylformamide (3 ml) according to the general procedure and was obtained after flash chromatography (petroleum ether/ethyl acetate 1/1 v/v) as a yellowish oil (0.28 g, 84%).

Example 4 cilazapril 1-acetoxyethyl ester (4)

(1S,9S)-1-(acetoxy)ethyl 9-[[(1S)-1-ethoxycarbonyl-3-phenylpropyl]amino]-10-oxooctahydro-1H-pyridazino[1,2-a][1,2]diazepine-1-carboxylate (4)

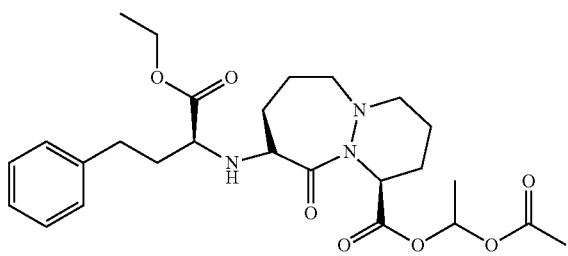

Cilazapril 1-acetoxyethyl ester (4) was prepared according to the general procedure using cilazapril (0.60 mmol, 0.25 g), $K_2CO_3$ (0.72 mmol, 0.10 g) and 1-chloroethyl acetate (0.78 mmol, 0.11 g) in anhydrous dimethylformamide (3 ml) and was obtained after flash chromatography (petroleum ether/ethyl acetate 5/4-1/2 v/v) as a pale yellow oil (0.18 g, 70%).

Example 5 cilazapril 1-(2,2-dimethylpropanoyloxy)ethyl ester (5)

(1S,9S)-1-(2,2-dimethylpropanoyloxy)ethyl 9-[[(1S)-1-ethoxycarbonyl-3-phenylpropyl]amino]-10-oxooctahydro-1H-pyridazino[1,2-a][1,2]diazepine-1-carboxylate, (5)

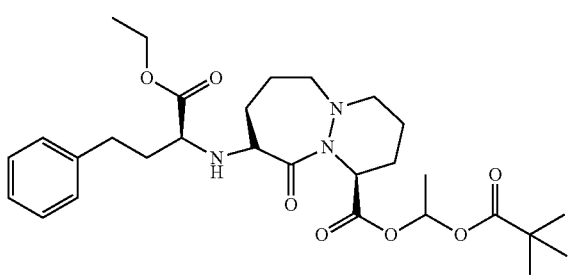

Cilazapril 1-(2,2-dimethylpropanoyloxy)ethyl ester (5) was prepared from cilazapril (0.60 mmol, 0.25 g), $K_2CO_3$ (0.72 mmol, 0.10 g) and 1-chloroethyl 2,2-dimethylpropanoate (0.78 mmol, 0.14 g) in anhydrous dimethylformamide (3 ml) according to the general procedure and was obtained after flash chromatography (petroleum ether/ethyl acetate 1/1 v/v) as a pale yellow oil (0.29 g, 87%).

Example 6 cilazapril morpholinoethyl ester (6)

(1S,9S)-2-morpholinoethyl 9-[[(1S)-1-ethoxycarbonyl-3-phenylpropyl]amino]-10-oxooctahydro-1H-pyridazino[1,2-a][1,2]diazepine-1-carboxylate (6)

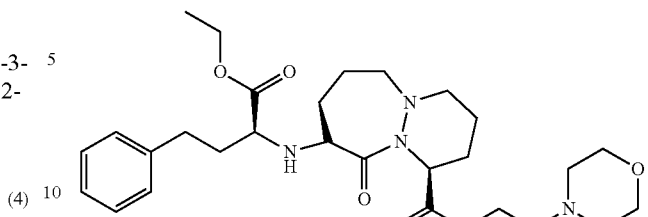

To a solution of cilazapril (1 eq, 2.4 mmol, 1.00 g) in anhydrous dichloromethane (5 ml) a catalytic amount of 4-(dimethylamino)pyridine and 4-(2-hydroxyethyl)morpholine (1 eq, 2.40 mmol, 0.29 ml) were added. A solution of N,N'-dicyclohexylcarbodiimide (1.1 eq, 2.64 mmol, 0.55 g) in anhydrous dichloromethane (2 ml) was added dropwise at 0° C. under an atmosphere of argon. The reaction mixture was stirred at 0° C. for one hour and overnight at room temperature. Solids were removed by filtration. Rotary evaporation of the filtrate gave the crude product which was subjected to flash chromatography (petroleum ether/ethyl acetate 1/3+0.5% $NEt_3$ v/v) to yield cilazapril morpholinoethyl ester (6) as yellow oil (0.91 g, 72%).

Example 7 cilazapril 1-(2-morpholinoacetoxy)ethyl ester (7)

(1S,9S)-1-(2-morpholinoacetoxy)ethyl 9-[[(1S)-1-ethoxycarbonyl-3-phenylpropyl]amino]-10-oxooctahydro-1H-pyridazino[1,2-a][1,2]diazepine-1-carboxylate (7)

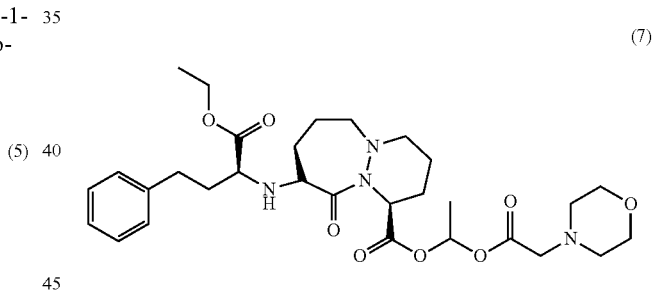

To a solution of the trifluoroacetic acid salt of 2-morpholinoacetic acid (2 eq, 1.88 mmol, 0.49 g) in anhydrous dimethylformamide (6 ml) was added $Cs_2CO_3$ (4 eq, 3.76 mmol, 1.23 g). A solution of (1S,9S)-9-[(S)-1-ethoxycarbonyl-3-phenylpropylamino)-10-oxooctahydro-1H-pyridazino[1,2-a][1,2]diazepine-1-carboxylic acid 1-chloroethyl ester (1 eq, 0.94 mmol, 0.45 g) in anhydrous dimethylformamide (1 ml) was added dropwise. The mixture was stirred for 7 h at 40° C. and overnight at room temperature. The solvent was evaporated under reduced pressure and the residue was taken up in ethyl acetate/$H_2O$ 1/1 v/v. The layers were separated and the aqueous phase was extracted with ethyl acetate twice. The combined organic phases were washed with brine, dried over anhydrous $MgSO_4$, filtered and evaporated to dryness. Flash chromatography (petroleum ether/ethyl acetate 1/1 to 1/2 v/v+$NH_3$) of the crude material yielded cilazapril 1-(2-morpholinoacetoxy)ethyl ester (7) as a yellow oil (0.17 g, 31%).

Examples of TTS Manufacture

In the examples below, cilazapril 1-(ethoxycarbonyloxy)ethyl ester (1), cilazapril 1-(cyclohexyloxycarbonyloxy)ethyl ester (2) and cilazapril 2-morpholinoethyl ester (6) are named cilazapril prodrug (1), cilazapril prodrug (2) and cilazapril prodrug (6) respectively.

Example 8

Manufacture of a TTS Comprising Cilazapril Prodrug (1)

The components as indicated below were used:

| Contents | Amount in % by weight |
| --- | --- |
| (1) | 10 |
| BioPSA ® Hex 7-4302 (PSA) | 90 |

In a stirred vessel, the cilazapril prodrug (1) was dissolved in ethyl acetate as solvent. After the mixture became clear, the pressure sensitive adhesive (BioPSA® Hex 7-4302, Dow Corning) was added and the mixture was stirred for about 1 h and controlled visually, whether all solids were dissolved. The solution was then coated on a transparent, fluorosiliconized polyester foil, which served as a release liner. The solvents were removed by drying with heated air, which was streamed over the wet coating. The adhesive coating was then covered with a polyester foil (PET) of a thickness of 15 µm. An area of 10 cm$^2$ was then punched out by appropriate cutting tools. Subsequently the TTS was packed into air tight sachets.

Example 9

Manufacture of a TTS Comprising Cilazapril Prodrug (2)

The components as indicated below were used:

| Contents | Amount in % by weight |
| --- | --- |
| (2) | 10 |
| BioPSA ® Hex 7-4302 (PSA) | 90 |

In a stirred vessel, the cilazapril prodrug (2) was dissolved in ethyl acetate as solvent. The further steps were carried out as in Example 1.

Example 10

Manufacture of a TTS Comprising Cilazapril Prodrug (6)

The components as indicated below were used:

| Contents | Amount in % by weight |
| --- | --- |
| (6) | 10 |
| BioPSA ® Hex 7-4302 (PSA) | 90 |

In a stirred vessel, the cilazapril prodrug (6) was dissolved in ethyl acetate as solvent. The subsequent steps were carried out as in Example 1.

Example 11

Manufacture of the Comparative TTS Comprising Cilazapril

The components as indicated below were used:

| Contents | Amount in % by weight |
| --- | --- |
| Cilazapril | 10 |
| BioPSA ® Hex 7-4302 (PSA) | 90 |

In a stirred vessel, cilazapril was dissolved in ethyl acetate as solvent. The subsequent steps were carried out as in Example 1.

The stability of the cilazapril prodrugs (1) and (2) in therapeutic transdermal systems was controlled at 25° C./60% relative humidity and compared with the cilazapril in a TTS having the same adhesive layer.

TABLE 5

| Storage time | Storage conditions | prodrug (1) assay [%] | prodrug (2) assay [%] | prodrug (6) assay [%] | cilazapril assay [%] |
| --- | --- | --- | --- | --- | --- |
| 0 months | uncontrolled | 99.3 | 100.0 | 98.1 | 99.8 |
| 9 months | 25° C./60% relative humidity | 98.0 | 98.3 | 94.7 | 97.0 |

Table 5 shows that the prodrugs of the invention in TTS are sufficiently stable at 25° C./60% relative humidity.

Moreover, the TTSs with the prodrugs (1), (2) and (6) were examined with regard to crystallization. After 14 months, none of the TTS showed crystallization.

Furthermore the permeability of the prodrugs through the skin was measured by in vitro skin permeation. The in vitro skin permeation of the prodrugs (1), (2) and (6) and of cilazapril through human skin was evaluated using the TTS as prepared in any one of examples 8, 9, and 11.

The flux was determined by using a two-compartment diffusion cell with a section of human skin mounted between the cell halves. A TTS was adhered to one side of the skin and a drug-receiving medium was placed on the receptor-side of the cell. The apparatus was placed in a water bath maintained at 32±1° C. Samples of the receptor medium were collected over a period of 96 hours for HPLC analysis of drug concentration.

It can be seen from FIG. 1 that the TTSs containing cilazapril 1-(ethoxycarbonyloxy)-ethyl ester (1), cilazapril 1-(cyclohexyloxycarbonyloxy)ethyl ester (2) or cilazapril morpholinoethyl ester (6) according to the invention provide an increase in in vitro skin flux compared to the cilazapril TTS. Accordingly, the rate at which the active ingredient passes through the skin including the *Stratum corneum*, the epidermis, and the dermis is increased. Thus, the systemic availability of the cilazapril prodrug is improved with the compounds of the present invention.

The invention claimed is:
1. A compound selected from the group consisting of:
(1S,9S)-1-(ethoxycarbonyloxy)ethyl 9-[[(1S)-1-ethoxycarbonyl-3-phenylpropyl]amino]-10-oxooctahydro-1H-pyridazino[1,2-a][1,2]diazepine-1-carboxylate;

(1S,9S)-1-(cyclohexyloxycarbonyloxy)ethyl 9-[[(1S)-1-ethoxycarbonyl-3-phenylpropyl]amino]-10-oxooctahydro-1H-pyridazino[1,2-a][1,2]diazepine-1-carboxylate;

(1S,9S)-2-morpholinoethyl 9-[[(1S)-1-ethoxycarbonyl-3-phenylpropyl]amino]-10-oxooctahydro-1H-pyridazino[1,2-a][1,2]diazepine-1-carboxylate;

(1S,9S)-1-(isopropyloxycarbonyloxy)ethyl 9-[[(1S)-1-ethoxycarbonyl-3-phenylpropyl]amino]-10-oxooctahydro-1H-pyridazino[1,2-a][1,2]diazepine-1-carboxylate;

(1S,9S)-1-(acetoxy)ethyl 9-[[(1S)-1-ethoxycarbonyl-3-phenylpropyl]amino]-10-oxooctahydro-1H-pyridazino[1,2-a][1,2]diazepine-1-carboxylate;

(1S,9S)-1-(2,2-dimethylpropanoyloxy)ethyl 9-[[(1S)-1-ethoxycarbonyl-3-phenylpropyl]amino]-10-oxooctahydro-1H-pyridazino[1,2-a][1,2]diazepine-1-carboxylate; and (1S,9S)-1-(2-morpholinoacetoxy)ethyl 9-[[(1S)-1-ethoxycarbonyl-3-phenylpropyl]amino]-10-oxooctahydro-1H-pyridazino[1,2-a][1,2]diazepine-1-carboxylate.

2. A transdermal therapeutic system comprising at least one compound according to claim 1.

3. The transdermal therapeutic system according to claim 2, further comprising:
   a) at least one pressure sensitive adhesive,
   b) a backing layer, and
   c) a release liner.

4. The transdermal therapeutic system according to claim 3, wherein the compound is dissolved or suspended in the pressure sensitive adhesive(s).

5. The transdermal therapeutic system according to claim 3, wherein the pressure sensitive adhesive is present in at least one adhesive layer.

6. The transdermal therapeutic system according to claim 4, wherein the pressure sensitive adhesive is present in at least one adhesive layer.

7. The transdermal therapeutic system according to claim 3, further comprising an adhesive layer which does not comprise the compound of claim 1.

8. The transdermal therapeutic system according to claim 4, further comprising an adhesive layer which does not comprise the compound of claim 1.

9. The transdermal therapeutic system according to claim 5, further comprising an adhesive layer which does not comprise the compound of claim 1.

10. The transdermal therapeutic system according to claim 5, wherein the at least one of the adhesive layer further comprises at least one penetration and/or permeation enhancer.

11. The transdermal therapeutic system according to claim 5, wherein the at least one of the adhesive layer further comprises at least one tackifier.

12. The transdermal therapeutic system according to claim 5, wherein the at least one of the adhesive layer further comprises at least one crystallization inhibitor.

13. The transdermal therapeutic system according to claim 3, wherein the pressure sensitive adhesive is silicon, polyacrylate and/or polyisobutylene based.

14. The transdermal therapeutic system according to claim 3, further comprising a coverpatch.

15. A method of treating hypertension and/or congestive heart failure comprising treating a patient with hypertension and/or congestive heart failure by applying a transdermal therapeutic system to the skin of the patient, wherein the transdermal therapeutic system comprises at least one compound according to claim 1.

16. The method according to claim 15, wherein the transdermal therapeutic system comprises:
   a) at least one pressure sensitive adhesive,
   b) a backing layer, and
   c) a release liner.

17. The method according to claim 16, wherein the compound is dissolved or suspended in the pressure sensitive adhesive(s).

18. The method according to claim 17, wherein the pressure sensitive adhesive is present in at least one adhesive layer.

19. A pharmaceutical composition comprising a pharmaceutically effective amount of at least one compound according to claim 1.

20. A method of treating hypertension and/or congestive heart failure comprising treating a patient with hypertension and/or congestive heart failure by delivering at least one compound according to claim 1 to the patient.

* * * * *